United States Patent [19]
Hanaki

[11] Patent Number: 6,074,063
[45] Date of Patent: Jun. 13, 2000

[54] OPHTHALMIC APPARATUS FOR PHOTOGRAPHING AN ANTERIOR PART OF AN EYE

[75] Inventor: Hirohiko Hanaki, Gamagori, Japan

[73] Assignee: Nidek Co., Ltd., Aichi, Japan

[21] Appl. No.: 09/239,676

[22] Filed: Jan. 29, 1999

[30] Foreign Application Priority Data

Jan. 30, 1998 [JP] Japan .................................. 10-034036

[51] Int. Cl.⁷ ..................................................... A61B 3/10
[52] U.S. Cl. ........................................................... 351/206
[58] Field of Search .................................... 351/205, 206, 351/207, 208, 210, 211, 212; 396/18

[56] References Cited

U.S. PATENT DOCUMENTS

| | | | |
|---|---|---|---|
| 4,711,540 | 12/1987 | Yoshino et al. | 351/214 |
| 4,711,541 | 12/1987 | Yoshino et al. | 351/214 |
| 5,202,708 | 4/1993 | Sasaki et al. | 351/206 |
| 5,309,186 | 5/1994 | Mizuno | 351/212 |
| 5,512,965 | 4/1996 | Snook | 351/205 |
| 5,713,047 | 1/1998 | Kohayakawa | 351/206 |
| 5,757,462 | 5/1998 | Nanjo | 351/206 |
| 5,864,382 | 1/1999 | Soya et al. | 351/206 |
| 5,886,768 | 4/1999 | Knopp et al. | 351/212 |

FOREIGN PATENT DOCUMENTS

| | | |
|---|---|---|
| 43 21 796 | 1/1994 | Germany . |
| 60-145120 | 7/1985 | Japan . |
| 60-145121 | 7/1985 | Japan . |
| 60-160941 | 8/1985 | Japan . |
| 61-45721 | 3/1986 | Japan . |
| 61-45724 | 3/1986 | Japan . |
| 61-45725 | 3/1986 | Japan . |
| 9-313446 | of 1997 | Japan . |
| 10-33482 | 2/1998 | Japan . |
| 2 112 171 | 7/1983 | United Kingdom . |

OTHER PUBLICATIONS

Official European Search Report dated May 4, 1999 (2 pages).

*Primary Examiner*—George Manuel
*Attorney, Agent, or Firm*—Finnegan, Henderson, Farabow, Garrett & Dunner, L.L.P.

[57] ABSTRACT

An ophthalmic apparatus for photographing an anterior part of an eye to be examined, the apparatus comprising a sectional image photographing optical system for photographing a sectional image of the anterior part of the eye, a rotating device for rotating the sectional image photographing optical system, a retroillumination image photographing optical system for photographing a retroillumination image of the anterior part of the eye, a determining device for obtaining a rotation angle that the sectional image photographing optical system is to be rotated by the rotating device based on the retroillumination image photographed by the retroillumination photographing optical system and a controlling device for controlling operation of the rotating device based on the rotation angle obtained by the determining device.

12 Claims, 4 Drawing Sheets

OPHTHALMIC APPARATUS FOR PHOTOGRAPHING AN ANTERIOR PART OF AN EYE

BACKGROUND OF THE INVENTION

1. Field of the Invention

The present invention relates to an ophthalmic apparatus for photographing a retroillumination image or a sectional image of an anterior part of an eye to be examined.

2. Description of Related Art

Conventionally, there are two major ways to evaluate cataract. One is to project illumination light through a pupil of an eye to be examined. The scattered light from a fundus of the eye illuminates a crystalline lens and thereby observing a retroillumination image of the crystalline lens from the front. This manner enables to observe development of cataract throughout the crystalline lens.

The other is to optically cut the eye to be examined by slit light and then observe an anterior part of the eye by a photographing optical system arranged in accordance with the Scheimpflug's principle. This manner allows to obtain location of an opaque area in the crystalline lens and degree of its opacity.

Suggested in consideration of the above is an apparatus which is capable of photographing both a retroillumination image as well as a sectional image of the anterior part of the eye. When utilizing this type of apparatus, an irradiation system and a photographing system are switched upon photographing a retroillumination image and photographing a sectional image.

In a conventional apparatus, however, there is no correlation between the retroillumination photography and the sectional image photography and thus it is left to an examiner's judgement. That is to say, the examiner decides a rotation angle at which the section of the anterior part of the eye is to be photographed entirely depending on his intuition and experience. Therefore, there may be cases where a required picture image can not be obtained or photography has to be repeated over and over, which imposes excessive burden on the examinee.

SUMMARY OF THE INVENTION

The present invention has been made in view of the above circumstances and has an object to overcome the above problems and to provide an ophthalmic apparatus for photographing an anterior part of an eye to be examined which is able to obtain an appropriate sectional image easily.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an ophthalmic apparatus for photographing an anterior part of an eye to be examined, the apparatus comprises a sectional image photographing optical system for photographing a sectional image of the anterior part of the eye, rotating means for rotating the sectional image photographing optical system, a retroillumination image photographing optical system for photographing a retroillumination image of the anterior part of the eye, determining means for obtaining a rotation angle that the sectional image photographing optical system is to be rotated by the rotating means based on the retroillumination image photographed by the retroillumination image photographing optical system and controlling means for controlling operation of the rotating means based on the rotation angle obtained by the determining means.

According to the present invention, the examiner can easily obtain a sectional image photographed along an intended part of the eye.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
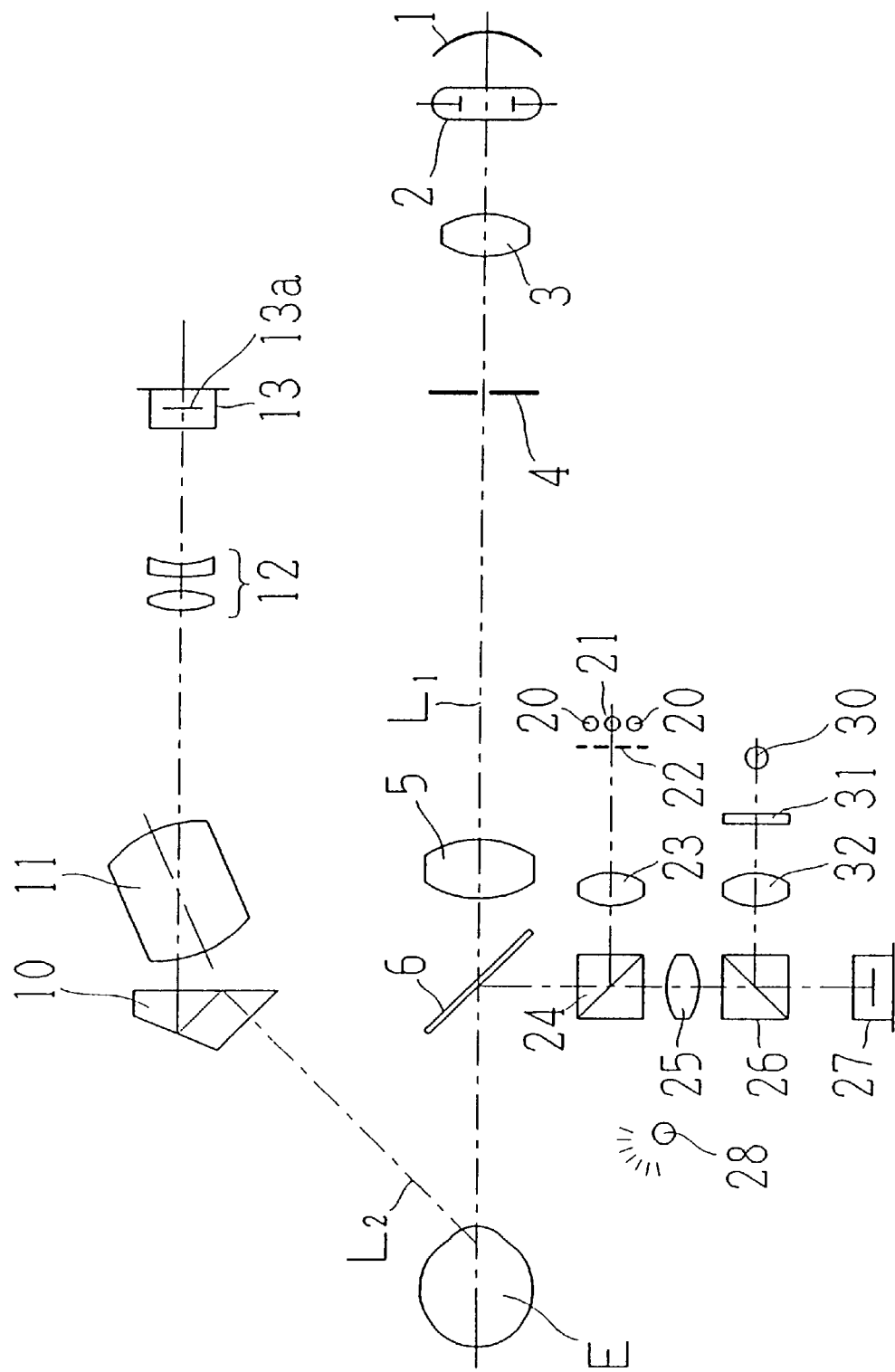
FIG. 1 is a view showing constructions of optical systems of a photographing unit 100 in a preferred embodiment of the present invention.

A detailed description of one preferred embodiment of an ophthalmic apparatus for photographing an anterior part of an eye embodying the present invention will now be given referring to the accompanying drawings. FIG. 1 is a view showing constructions of optical systems of a photographing unit 100 in the apparatus of the preferred embodiment of the present invention.

<Slit Light Projecting Optical System>

Reference numeral 1 denotes a reflecting mirror, 2 is a flash lamp for photography, 3 is a condenser lens, 4 is a slit aperture diaphragm, 5 is a projecting lens, and 6 is a dichroic mirror which is disposed slantingly on an optical axis L1 of a slit light projecting optical system. The slit aperture diaphragm 4 is a variable diaphragm of which slit can be lengthened or shortened, and the dichroic mirror 6 has characteristics of transmitting most of visible light but reflecting infrared light.

Photography is performed by utilizing scattered light from biomolecules of a cornea and a crystalline lens of an eye E to be examined which is cut optically. As wavelength of the light becomes shorter, the scattering of the light becomes greater, thereby increasing a capacity for detecting. Yet, it may be preferred to use a moderate white light, because an optical toxicity would be more harmful to an eyeball within a ultraviolet region.

<Slit-Section Photographing Optical System>

Reference numeral L2 denotes a photographic optical axis of a slit-section photographing optical system. 10 is a deflection angle prism for changing a direction of the photographic optical axis L2. 11 is a photographing lens, 12 is an anamorphic lens, 13 is a CCD camera for photographing a section. The photographic optical axis L2 is disposed so as to intersect the optical axis L1 at an inclination angle of 45° near a point where an alignment target image, which will be described later, is formed when an alignment is almost completed by observing from in front. The photographing lens 11 is arranged inclined to the photographic optical axis of which direction can be changed by the deflection angle prism 10 so as to fulfill the Scheimpflug's principle. That is to say, the photographing lens 11 is arranged so that, without the deflection angle prism 10, an extension of an imaging plane 13a of the CCD camera 13 and an extension of a slit-section of the anterior part of the eye E being optically cut by the slit illumination light would intersect on a extension of a principal plane of the photographing lens 11. According to this optical arrangement, a sectional image photographed by the CCD camera 13 (an image of the slit-section formed around a collective point of the slit light by the scattered light from biomolecules of the anterior part of the eye) is allowed to hold a focal depth which focuses on the approximately entire sectional image.

<Alignment Target Projecting Optical System and Retroillumination Light Projecting Optical System>

Reference numeral 20 denotes a couple of light sources for alignment which project an alignment target from the front the eye E (a direction of a visual axis). The light sources 20 are also utilized as fixation light sources and therefore emit infrared light which partially includes visible light. Each of the light sources 20 is disposed for a right eye and a left eye at positions where suitably correspond to inclinations of the visual axes of the right eye and the left eye respectively. 21 is a light source for photographing a retroillumination image which emits light of a wavelength in a infrared region. 22 is a target plate having pin-hole apertures along projection optical axes of the light sources 20 and 21, 23 is a projecting lens and 24 is a beam splitter. The target plate 22 is positioned near a front focal point of the projecting lens 23. Alignment light projected onto the eye E is reflected from the cornea in a manner of surface reflection, and thereby forming a target image of the target plate 22 at a distance equal to one half of a radius of a corneal curvature away from a corneal vertex toward inside of the eye E.

<Front Photographing Optical System for the Anterior Part of the Eye>

Reference numeral 25 denotes a photographing lens, 26 is a beam splitter, and 27 is a CCD camera for observing a front side of having its sensitivity within an infrared region. 28 is an infrared-illumination light source for illuminating the anterior part of the eye E. The image of the anterior part of the eye E illuminated by the infrared-illumination light source 28 is first reflected by the dichroic mirror 6, successively goes through the beam splitter 24, the photographing lens 25 and the beam splitter 26 and then photographed by the CCD camera 27.

<Front Reticle Optical System>

Reference numeral 30 denotes a reticle plate illuminating light source, 31 is a reticle plate in which an aiming mark is formed and 32 is a reticle projecting lens. The reticle plate illuminating light source 30 illuminates the aiming mark formed in the reticle plate 31. After passing through the reticle projecting lens 32, the image of the aiming mark is reflected by the beam splitter 26 and then photographed by the CCD camera 27 along with the image of the anterior part of the eye and the target image.

In the above-described optical systems, the slit-section photographing optical system and the aperture diaphragm 4 are structured so as to be rotated about the optical axis L1 by an unillustrated rotation mechanism. This allows the sectional image to be photographed at any desired angle. For this rotation mechanism, various known mechanisms may be applied. One example is to provide a gear for a housing which stores optical systems therein. Rotation is accomplished by a rotation pulse motor provided with a pinion which fits the gear.

Figure 2:
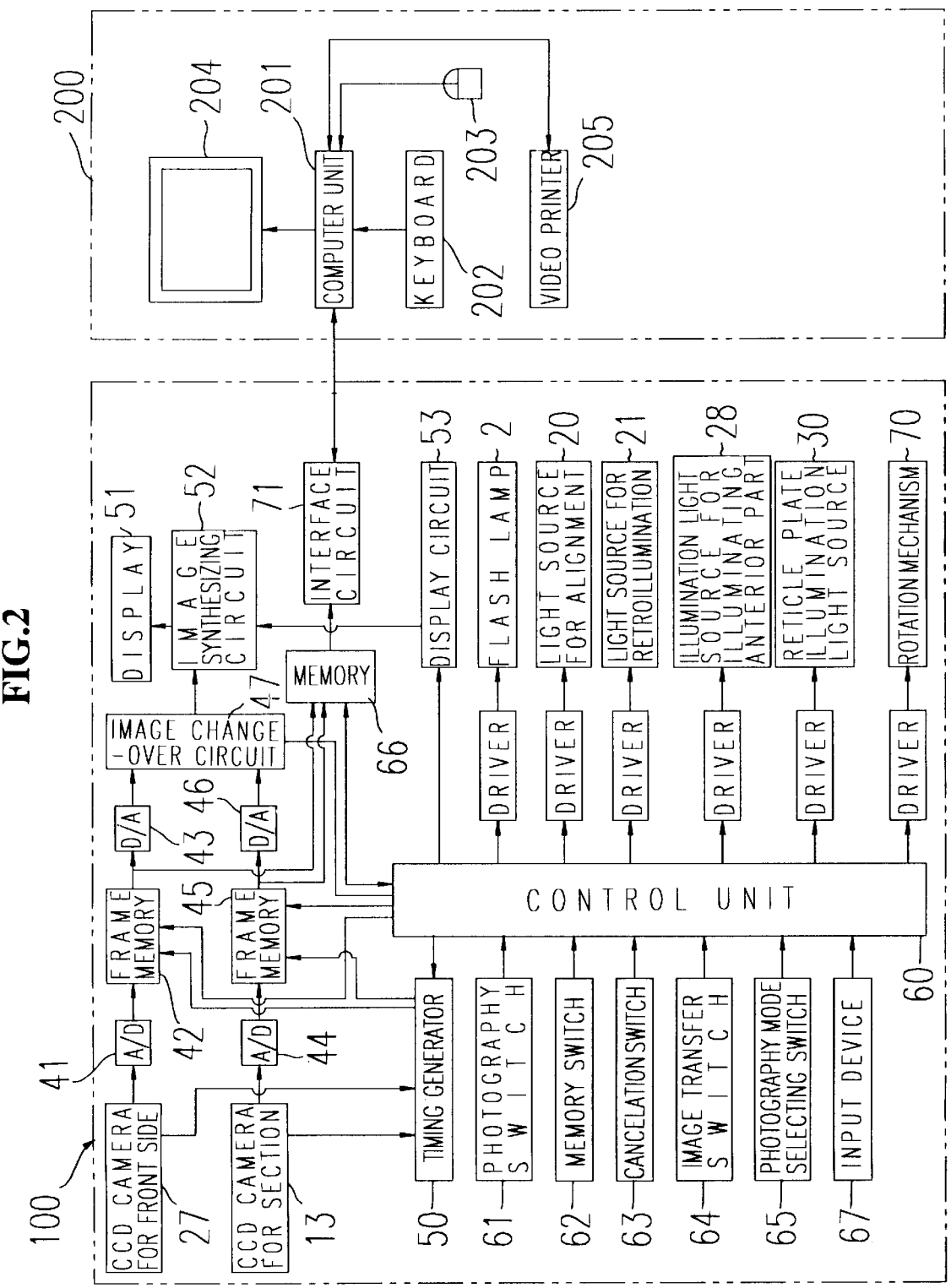
FIG. 2 is a view showing constructions of signal processing of the photographing unit 100 and of an image analyzing unit 200 in the embodiment of the present invention.

FIG. 2 is a view showing constructions of control systems of the photographing unit 100 and an image analyzing unit 200.

<Corneal Section Photographing Unit>

A video signal from the CCD camera 27 for observing a front side is digitized by an A/D converting circuit 41 and then inputted to a frame memory 42 being synchronized with a signal generated by a timing generator 50. The picture signal inputted to the frame memory 42 is converted to a video signal by a D/A converting circuit 43 and then transmitted to an image change-over circuit 47.

In the same manner, a video signal from the CCD camera 13 for photographing a section is digitized by an A/D converting circuit 44 and then inputted to a frame memory 45. The picture signal inputted to the frame memory 45 is converted to a video signal by a D/A converter 46 and then transmitted to the image change-over circuit 47.

Reference numeral 52 is an image synthesizing circuit. The image synthesizing circuit 52 synthesizes various information displays generated by a display circuit 53 with picture images from the CCD 27 or 13 so as to display on a display 51.

The retroillumination image or the sectional image of the anterior part of the eye which is frozen into the frame memory 42 or 45 upon photographing will be stored into a memory 66 by operating a memory switch 62. At an input from an image transfer switch 64, the image is then transferred to the image analyzing unit 200 via an interface circuit 71.

<Image Analyzing Unit>

Reference numeral 201 denotes a computer unit which analyzes pictorial data on the sectional image inputted from the photographing unit 100 through image processing. The computer unit 201 comprises memory for storing the pictorial data and memory for storing an analytical program to carry out the image analysis therein. A keyboard 202 and a mouse 203 are connected to the computer unit 201 to input operating instructions. For the hardware of the computer unit 201, the keyboard 202 and the mouse 203, it may be suitable to use a commercially available computer. 204 is a color display which displays the sectional image or the analysis thereon and 205 is a video printer.

Hereinafter, a description will be made regarding operations of the ophthalmic apparatus for photographing the anterior part of the eye which has the above-described configuration.

<Photography of the Retroillumination Image of the Anterior Part of the Eye>

An examiner selects a retroillumination image photography mode with the use of a photography mode selecting switch 65 and then places the eye E at a predetermined position in the photographing unit 100. To correct deviation between the visual axis and the optical axis, which allows the right eye and left eye to be photographed under even conditions, one of the light sources 20 which corresponds to the eye being photographed is selectively lit. The eye E is fixed to the target plate 22 provided in the alignment target projecting optical system which at this time functions as the fixation optical system. Light emitted from the light source 20 illuminates the target plate 22. After passing though the lens 23 and thereby being parallel light, the alignment light is first reflected by the beam splitter 24 and then by the dichroic mirror 6 so as to enter into the eye E along the optical axis L1.

Part of the alignment light projected by the alignment target projecting optical system is reflected by the cornea. The reflected light from the cornea, along with the front image of the anterior part of the eye E illuminated by the light source 28, will be photographed by the CCD 27 via the dichroic mirror 6, the beam splitter 24, the lens 25 and the beam splitter 26. The front image of the anterior part of the eye and the alignment target image photographed by the CCD 27 are displayed on the display 51.

The examiner moves a photographing optical system provided in the photographing unit 100 in vertical and horizontal directions relative to the eye E by operating an unillustrated joystick or the like and thereby making predetermined alignment of the alignment target image and the reticle (aiming mark) image. Here, the optical axis of the photographing unit 100 is brought into coincidence with the visual axis of the eye E. Further, the photographing unit 100 is shifted in a back-and-forth direction to a point where the alignment target image becomes the smallest and clearest to accomplishes alignment of a working distance.

When the two axes are brought into coincidence with each other and the alignment of the working distance is completed, the examiner depresses a photography switch 61. A control unit 60 stores a position where the switch 61 is inputted (a position where the focus is on a corneal luminance point) as a reference point. The control unit 60, in response to the input signal from the switch 61, turns on the light source 21 and turns off the light sources 20, 28 and 30.

Light emitted from the light source 21 passes through the target plate 22 and made to be parallel light by passing through the projecting lens 23. Thereafter, the light is reflected by the beam splitter 24 and then by the dichroic mirror 6 so as to enter the eye E. The light entered the eye E is reflected by the fundus so as to illuminate the anterior part of the eye from a rear direction (from a direction of the fundus).

In the same manner as the front image of the anterior part of the eye, the retroillumination image of the anterior part of the eye formed by the illumination light from a rear direction is photographed by the CCD 27 via the dichroic mirror 6, the beam splitter 24, the lens 25 and the beam splitter 26 and then displayed on the display 51.

Displacement in a direction of the optical axis L1 from the reference point is detected by unillustrated moving amount detecting means and a distance to a position of the image being photographed at that time is displayed on the display 51 in 0.1 mm along with the retroillumination image. The distance in the direction of the optical axis L1 displayed on the display 51 helps the examiner to recognize the approximate focal point. In addition, it is also utilized to specify a photographing position upon examining change with time.

With observing the retroillumination image and the focal point in the direction of the optical axis L1 displayed on the display 51, the examiner moves the unillustrated joystick in a back-and-forth direction thereby determining a photographing position which attains a focus on an opaque area. When the photographing position is determined, the examiner depresses the switch 61 again. Responsive to the input signal from the switch 61, the control unit 60 freezes the retroillumination image of the anterior part of the eye in the frame memory 42 via the timing generator 50. The image frozen in the frame memory 42 is displayed on the display 51 via the circuit 47.

Upon checking the image displayed on the display 51, the examiner depresses the switch 62 if the image is satisfactory and if not, depresses a cancellation switch 63. In response to the input signal from the switch 62, the control unit 60 stores the pictorial data into the memory 66.

On the other hand, in the cases where the input signal from the switch 63 is transmitted, the control unit 60 cancels the photographed image which is frozen in the frame memory 42 and displays a front image of the eye E for observation on the display 51 based on the picture signal from the CCD 27. The examiner repeats the same operations as described above to redo the photography.

<Photography of the Sectional Image of the Anterior Part of the Eye>

Figure 3:
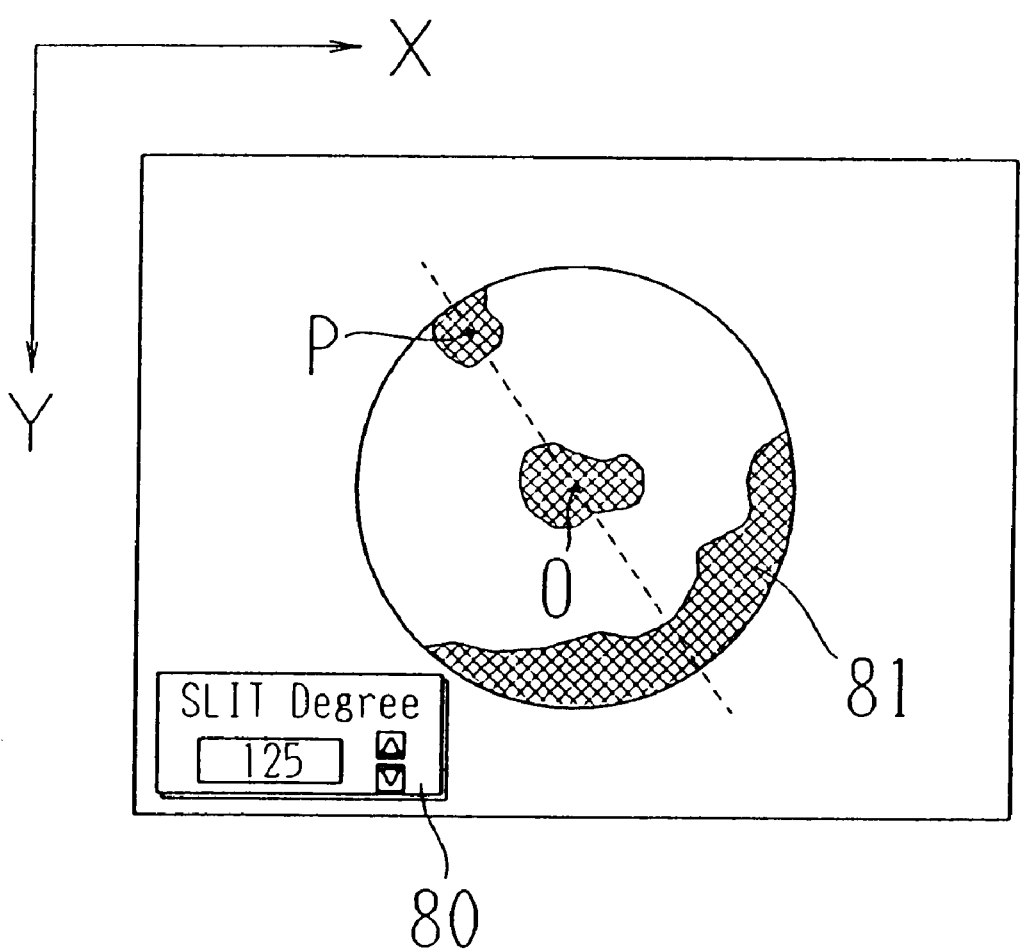
FIG. 3 is a view showing an example of a screen on a display.

In the cases where photography of the sectional image of the anterior part of the eye is carried out after completing the retroillumination image photography, the examiner depresses the photography mode selecting switch 65 to shift to a sectional image photography mode. In response to the input signal from the switch 65, the control unit 60 displays the retroillumination image stored in the memory 66 on the display 51 along with a rotation angle input window 80 (see FIG. 3).

With the use of an input device 67 such as a touch pen, a mouse or the like, the examiner designates a part to be photographed with observing opaque areas 81 in the retroillumination image displayed on the display 51. A point P denotes the point designated by the input device 67, and the point P is identified as the X, Y coordinates on the display 51.

In addition, a point corresponding to the optical axis L1 being a rotation center is denoted by a point O. By photographing a section along a doted line that connects the points P and O, the section which includes the designated point P is easily determined.

The control unit 60 calculates an angle of the section to be photographed from the point P which is designated by the input device 67 and also from the point O which corresponds to the optical axis L1 being the rotation center. The control unit 60 displays the obtained angle as a rotation angle on the window 80.

When the examiner confirms the section being photographed and depresses the switch 61, the control unit 60 drives a rotation mechanism 70 in accordance with the calculated rotation angle thereby rotating the section photographing optical system. At the completion of the rotation of the optical system, the front image of the eye E for observation is displayed on the display 51 in order to make alignment adjustment.

To correct the deviation of the alignment, the examiner carries out adjustment so as to bring the optical axis into coincidence with the visual axis of the eye E and also carries out the alignment of the working distance as in the case with the retroillumination image photography. Upon completing the alignment, the examiner depresses the switch 61, so that the flash lamp 2 emits light. At this time, the slit-section photographing optical system and the diaphragm 4 have been rotated about the optical axis L1 in accordance with the obtained angle upon the aforementioned retroillumination analysis. Therefore, it is easy to optically cut an opaque area so as to photograph an intended section.

The light emitted from the flash lamp 2 converges through the condenser lens 3 and illuminates the diaphragm 4. Being limited into a narrow slit by the diaphragm 4, the light transmits the dichroic mirror 6 via the lens 5 and is projected on the eye E thereby projecting a slit image of the diaphragm 4 on the anterior part of the eye E. As a result, the optic media of the anterior part (the cornea and the crystalline lens) is irradiated being optically cut by the light source which emits white light within a visible range.

The section of the cornea optically cut by the silt illumination is photographed by the CCD 13 via the prism 10, the lenses 11 and 12. The control unit 60 freezes the photographed image in the frame memory 45 with the use of the timing generator 50. Then, the control unit 60 sends a changeover signal to the circuit 47, thereby switching a display screen on the display 51 to the sectional image being frozen in the frame memory 45.

In the same manner as the case of the retroillumination image, the examiner checks the image displayed on the display 51 and depresses the switch 64 if the image is satisfactory and if not, depresses the cancellation switch 63. In response to the input signal from the switch 64, the control unit 60 transfers the pictorial data on the sectional image, along with the retroillumination image stored in the memory 66, to the computer unit 201 in the analyzing unit 200 via the circuit 71. The computer unit 201 stores the pictorial data transferred thereto into memory provided in the computer unit 201 and displays the image on the color display 204 along with menus for image analyses. The examiner performs various analyses of the image by selecting a menu item.

The display screens of the retroillumination image and the sectional image obtained in the aforementioned way can be printed out by operating the printer 205. In addition, it is also possible to store results of the analyses and the like and call up the stored results upon evaluating and comparing change with time.

The embodiment which has been described above is susceptible of various modifications. For example, instead of inputting a section for photographing on the display 51 provided in the photographing unit 100, the pictorial data may be transferred to the image analyzing unit 200 and then inputs a section to be photographed therein (the input may be done with the use of the keyboard 202, the mouse 203 or the like with reference to a display on the display 204).

In addition, the following corrective action may also be made in the cases where the retroillumination image is out of the alignment and photographed with its center being largely deviated from the rotation center upon retroillumination photography. Here, the image analyzing unit 200 detects the center of the retroillumination image (by calculating the pupil center or the like). With the detected center regarded to as the rotation center, the rotation angle is obtained with reference to the designated position by the input device.

Further modification may be made as follows. In the embodiment described above, the angle of the section to be photographed is obtained based on the input from the input means (the input device 67, the keyboard 202 or the like). In stead, the pictorial data of the retroillumination image may be transferred from the photographing unit 100 to the computer unit 201. The angle of the section for photography is obtained based on the image analysis done by the computer unit 201.

Figure 4A:
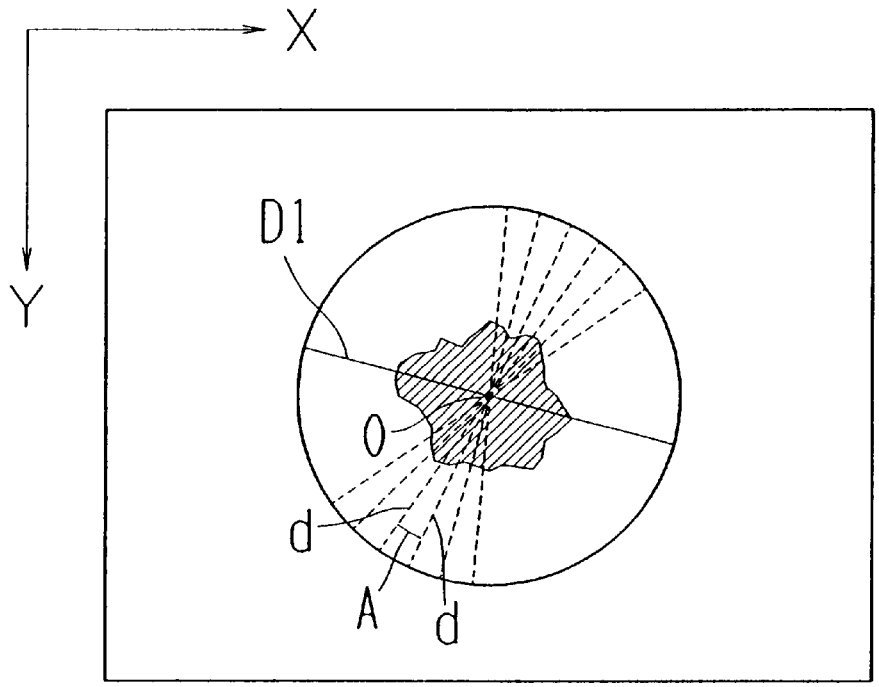
FIGS. 4A and 4B are views illustrating image analyses of a retroillumination image.

As shown in FIG. 4A, for example, detect optical density (intensity) along each detection line d having an interval of a predetermined angle A therebetween with the center at a point 0 which corresponds to the optical axis L1 being a rotation center (or a center of the retroillumination image). A detection line D1 having a largest range in which a predetermined optical density (intensity) is exceeded is detected and thereby determining the section for photography. Since opaque areas reflect the photographing light more than other part of the eye and thus, reflection by the opaque areas is more intense than that of the other part of the eye. Accordingly, by determining a detection line having the largest range in which the optical density (intensity) exceeds the predetermined level as a section to be photographed, a most widely spread opaque area can be photographed.

Figure 4B:
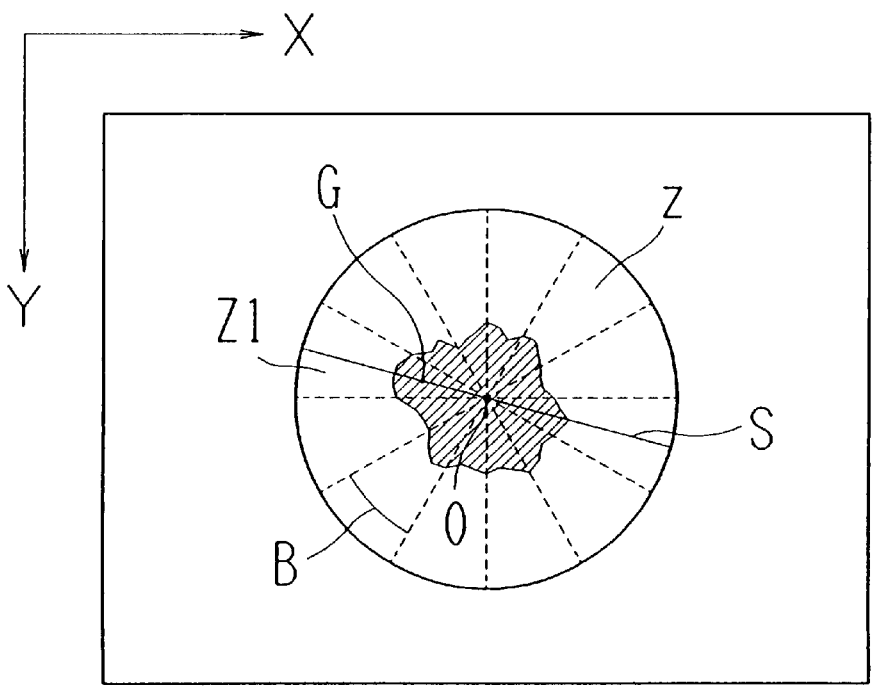

As another example is shown in FIG. 4B, it is also possible to detect optical density (intensity) of the retroillumination image in each detection area Z forming a predetermined angle of B with the center at a point O which corresponds to the optical axis L1 being a rotation center (or a center of the retroillumination image). An area Z1 having a greatest value thorough integration of the detected optical density (intensity) among each area is obtained. A point G denotes a center of gravity of the obtained area Z1. A line S which connects the points G and 0 determines the section to be photographed. As has been described above, the section to be photographed (or its angle) may be determined, based on the optical density (intensity) of the retroillumination image, in consideration of the given integrated value indicating degree of opacity or in consideration of the spread of the opaque area. The methods of image analyses are not limited to the above-described ones and various methods may be applied.

Regarding the angle of the section to be photographed, it is possible to make a modification so that the angle is determined either by the input device or by the image analysis selectively, or the angle may be determined by the image analysis first and then an intended angle may be added to the rotation.

In addition, the rotation of the section to be photographed may be driven and controlled manually instead of doing the same automatically as in the embodiment. The photographing optical system is not limited to the one based on the Scheimpflug's principle either.

Further, the present invention may be applied to observation of the cornea although observation of opaque areas due to cataract has been described in the embodiment. In the retroillumination image, opaque areas which exist not only in crystalline lens but also in the corneal part are observed. Hence, if the retroillumination image is photographed with focusing on the cornea, opaque areas exist therein are observed and a section to be photographed can be determined with reference to the opaque areas.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus for photographing an anterior part of an eye to be examined, the apparatus comprising:

a sectional image photographing optical system for photographing a sectional image of the anterior part of the eye;

rotating means for rotating said sectional image photographing optical system;

a retroillumination image photographing optical system for photographing a retroillumination image of the anterior part of the eye;

determining means for obtaining a rotation angle that said sectional image photographing optical system is to be rotated by said rotating means based on the retroillumination image photographed by said retroillumination image photographing optical system; and controlling means for controlling operation of said rotating means based on the rotation angle obtained by said determining means.

2. The ophthalmic apparatus according to claim 1, wherein said determining means comprises displaying means for displaying the retroillumination image photographed by said retroillumination image photographing optical system, designating means for designating a section of the anterior part of the eye to be photographed by said sectional image photographing optical system based on the retroillumination image displayed by said displaying means, and calculating means for calculating the rotation angle to be rotated by said rotating means in accordance with designation by said designating means.

3. The ophthalmic apparatus according to claim 2, wherein said designating means comprises inputting means for inputting an intended position on the retroillumination image displayed by said displaying means.

4. The ophthalmic apparatus according to claim 2, wherein said designating means comprises inputting means for inputting an intended position on the retroillumination image displayed by said displaying means; and wherein said calculating means calculates the rotation angle from the position inputted by said inputting means and a center of rotation made by said rotating means.

5. The ophthalmic apparatus according to claim 2, further comprising detecting means for detecting a center of the retroillumination image from the retroillumination image photographed by said retroillumination image photographing optical system; and wherein said designating means comprises inputting means for inputting an intended position on the retroillumination image displayed by said displaying means; and wherein said calculating means calculates the rotation angle from the position inputted by said inputting means and the center of the retroillumination image detected by said detecting means.

6. The ophthalmic apparatus according to claim 1, further comprising informing means for providing information about the sectional image photographed by said sectional image photographing optical system at the rotation angle determined by said determining means.

7. The ophthalmic apparatus according to claim 1, wherein said determining means comprises analyzing means for performing an image analysis of the retroillumination image photographed by said retroillumination image photographing optical system, designating means for designating a section of the anterior part of the eye to be photographed by said sectional image photographing optical system in accordance with a result of the image analysis by said analyzing means, and calculating means for calculating the rotation angle to be rotated by said rotating means in accordance with designation by said designating means.

8. The ophthalmic apparatus according to claim 7, wherein said analyzing means comprises detecting means for detecting optical density of the retroillumination image.

9. The ophthalmic apparatus according to claim 7, wherein said analyzing means comprises detecting means for detecting optical density of the retroillumination image along detection lines each of which intersects at the center of rotation made by said rotating means or at the center of the retroillumination image with a predetermined interval angle therebetween; and wherein said designating means, in accordance with a result detected by said detecting means, designates a detection line having a largest range in which the optical density exceeds a predetermined level as a line along which the section is photographed by said sectional image photographing optical system.

10. The ophthalmic apparatus according to claim 7, wherein said analyzing means comprises detecting means for detecting optical density of the retroillumination image in each detection area divided by lines each of which intersects at the center of rotation made by said rotating means or at the center of the retroillumination image with a predetermined interval angle therebetween, and integrating means for integrating the optical density detected in each detection area by said detecting means; and wherein said designating means comprises center of gravity calculating means, in accordance with a result obtained by said integrating means, for calculating a center of gravity of a detection area having highest optical density; and wherein said calculating means calculates the rotation angle from the center of gravity and the center of the rotation or the center of the retroillumination image.

11. The ophthalmic apparatus according to claim 1, wherein said controlling means drives and controls said rotating means electrically.

12. The ophtalmic apparatus according operating to claim 1, wherein said controlling means comprises operating means for driving said rotating means manually.

* * * * *

UNITED STATES PATENT AND TRADEMARK OFFICE
CERTIFICATE OF CORRECTION

PATENT NO. : 6,074,063
DATED : June 13, 2000
INVENTOR(S) : Hirohiko Hanaki

It is certified that error appears in the above-identified patent and that said Letters Patent is hereby corrected as shown below:

On the Title Page, Item [73], in the Assignee, "Aichi" should read --Gamagori--.

In Claim 12, col. 10, line 48, "ophtalmic" should read --ophthalmic--; and after "according", delete "operating".

Signed and Sealed this

Twenty-seventh Day of March, 2001

Attest:

NICHOLAS P. GODICI

Attesting Officer

Acting Director of the United States Patent and Trademark Office